United States Patent

Wolff et al.

[11] Patent Number: 6,028,199
[45] Date of Patent: Feb. 22, 2000

[54] HARDENERS FOR PHOTOGRAPHIC MATERIALS

[75] Inventors: Erich Wolff, Solingen; Peter Bergthaller, Bergisch Gladbach, both of Germany

[73] Assignee: Agfa-Gevaert NV, Mortsel, Belgium

[21] Appl. No.: 09/071,843

[22] Filed: May 1, 1998

Related U.S. Application Data

[63] Continuation of application No. 08/677,475, Jul. 10, 1996, abandoned.

[30] Foreign Application Priority Data

Jul. 20, 1995 [DE] Germany .......................... 195 26 468

[51] Int. Cl.[7] .................................................. C07D 211/70
[52] U.S. Cl. ............................................ 546/334; 546/330
[58] Field of Search ..................................... 546/330, 334, 546/323

[56] References Cited

U.S. PATENT DOCUMENTS

| | | | |
|---|---|---|---|
| 3,880,665 | 4/1975 | Himmelmann et al. | 96/111 |
| 4,063,952 | 12/1977 | Himmelmann et al. | 96/111 |
| 4,865,940 | 9/1989 | Schranz et al. | 430/138 |
| 5,229,260 | 7/1993 | Takamuki et al. | 430/527 |

*Primary Examiner*—Zinna Northington Davis
*Assistant Examiner*—Binta Robinson
*Attorney, Agent, or Firm*—Connolly Bove Lodge & Hutz LLP

[57] ABSTRACT

Hardeners for photographic materials, the binders of which substantially consist of gelatine, wherein the hardeners are carbamoylpyridinium salts, the amine components of which are derived from secondary amines, which amines are converted into photographically inert products by an intramolecular cyclisation reaction, improve photographic properties, even when the material is stored under extreme conditions.

6 Claims, No Drawings

HARDENERS FOR PHOTOGRAPHIC MATERIALS

This application is a continuation application of Ser. No. 08/677,475 which was filed Jul. 10, 1996, now abandoned.

Gelatine is used as a layer-forming binder in the production of photographic materials. It is necessary for photographic materials to be hardened so that the layers have sufficient scratch resistance for use in various devices together with sufficient stability in photographic processing baths even at elevated temperature.

Many different classes of compounds may be considered as hardeners; for example bisvinylsulphones, formaldehyde, hydroxydichlorotriazine, carbodiimides and carbamoylpyridinium salts. Some of these classes of compounds effect hardening by bifunctional crosslinking of free amino groups in the gelatine; these are described as conventional hardeners and are characterised in that the crosslinking reaction proceeds relatively slowly. At normal storage temperatures of 20 to 25° C., it takes approximately one week for final hardness to be achieved. Only once this state is achieved may the material finally be assessed and completed. Examples of this class of compounds include bisvinylsulphones and hydroxydichlorotriazines or the salts thereof.

In contrast, so-called instant hardeners harden on application. The hardening reaction is concluded immediately after application and the material has achieved its final state of hardness. This is in particular advantageous in the industrial production of photographic materials. Compounds which react with gelatine layers in accordance with this principle normally crosslink via free amino groups and free carboxyl groups of the various gelatine molecules, so forming true amide bonds. Examples of this class of compounds include carbodiimides and carbamoyl-pyridinium salts.

In this reaction, the carbamoylpyridinium salt yields a pyridine derivative, $CO_2$ and a secondary amine as secondary products.

It has now been found that, on storage in a heated or tropical cabinet, known carbamoylpyridinium salts bring about disadvantages with regard to the fog, gradation, light and dark stability of the photographic materials.

The object was to provide instant hardeners of the carbamoylpyridinium type with which the hardening reaction is concluded immediately after application but which do not exhibit the above-stated disadvantages.

It has now been found that this may be achieved with a particular type of carbamoylpyridinium salts.

The present invention accordingly provides hardeners for photographic materials, the binders of which substantially consist of gelatine, wherein the hardeners are carbamoylpyridinium salts, the amine components of which are derived from secondary amines, which are converted into photographically inert products by an intramolecular cyclisation reaction.

The hardeners are preferably of the formula (I)

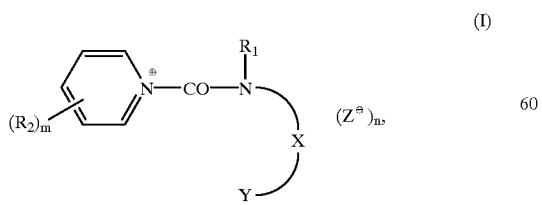

(I)

in which $R_1$ means an alkyl group, in particular with 1 to 4 C atoms, $R_2$ means a substituent, in particular an alkylene group with 1 to 4 C atoms substituted by $—SO_3^{\ominus}$ or $—COO^{\ominus}$ or an $—SO_3^{\ominus}$ or $—COO^{\ominus}$—group, Y means an atom or atomic group which may react with the N atom attached to $R_1$ to form a covalent bond, X means the remaining members of a chain of atoms, the number of members of which is calculated such that a 3- to 8-membered, preferably 5- to 7-membered ring is produced once Y has reacted with the nitrogen atom, $Z^{\ominus}$ means an anion, m means a number from 0 to 3 preferably 1 and n means 0 or 1, wherein n means 0 if $R_2$ is substituted by $SO_3^{\ominus}$ or $COO^{\ominus}$.

Y is preferably an ester group, an epoxide, a vinylsulphone group, isocyanate, Br, Cl, CN, methylol, urethane as well as a double bond activated by CN, $NO_2$, $CF_3$, CO, $SO_2$.

Preferred residues X are on the one hand alkylene groups with 2 to 5 C atoms and groups of the formula

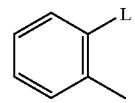

wherein L is linked to X and means a single bond, an alkylene group with 1 to 3 C atoms or $—SO_2—R_3$, wherein the $SO_2$ group is attached to the phenyl residue and $R_3$ denotes an alkylene group with 1 to 3 C atoms.

Suitable compounds of the formula (I) are, for example.

HM 1

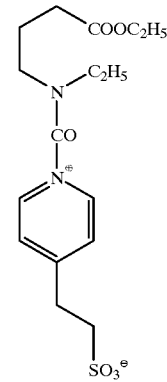

HM 2

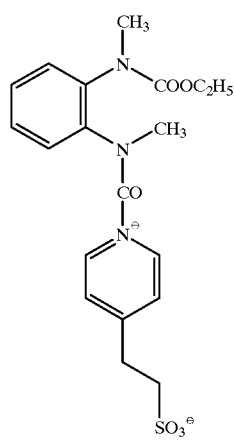

-continued

HM 3

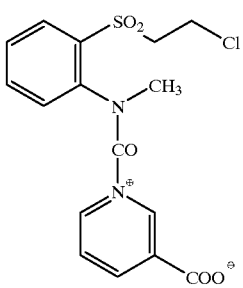

HM 4

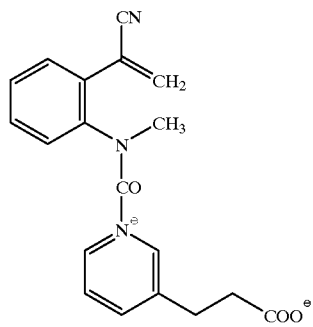

HM 5

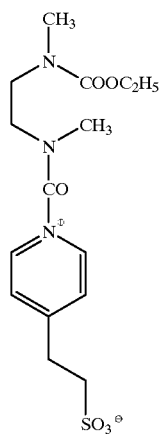

HM 6

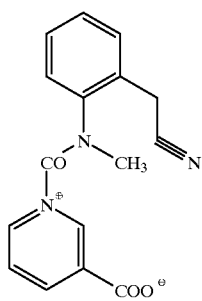

The hardeners according to the invention may be synthesised using known processes, for example It may, however, optionally be necessary during this process to introduce temporary protective groups, for example the trimethylsilyl residue, before phosgenation:

The novel hardeners are suitable for all photographic materials, the layer binder of which is predominantly (at least 50 wt. %) or exclusively gelatine.

Examples of colour photographic materials are colour negative films, colour reversal films, colour positive films, colour photographic paper, colour reversal photographic paper, colour sensitive materials for the dye diffusion transfer process or the silver dye bleaching process.

Photographic materials consist of a support onto which at least one photosensitive silver halide emulsion layer is applied. Suitable supports are in particular thin films and sheets. A review of support materials and of the auxiliary layers applied to the front and reverse thereof is given in *Research Disclosure* 37254, part 1 (1995), page 285.

Colour photographic materials conventionally contain at least one red-sensitive, one green-sensitive and one blue-sensitive silver halide emulsion layer optionally together with interlayers and protective layers.

Depending upon the nature of the photographic material, these layers may be differently arranged. This is described for the most important products:

Colour photographic films such as colour negative films and colour reversal films have on the support, in the stated sequence, 2 or 3 red-sensitive, cyan-coupling silver halide emulsion layers, 2 or 3 green-sensitive, magenta-coupling silver halide emulsion layers and 2 or 3 blue-sensitive yellow-coupling silver halide emulsion layers. The layers of identical spectral sensitivity differ with regard to their photographic sensitivity, wherein the lower sensitivity partial layers are generally arranged closer to the support than the higher sensitivity partial layers.

A yellow filter layer is conventionally arranged between the green-sensitive and blue-sensitive layers, which filter layer prevents blue light from penetrating the underlying layers.

Possible options for different layer arrangements and the effects thereof on photographic properties are described in *J. Int. Rec. Mats.*, 1994, volume 22, pages 183–193.

Colour photographic paper, which is generally substantially less photosensitive than a colour photographic film, conventionally has on the support, in the stated sequence, one blue-sensitive, yellow-coupling silver halide emulsion layer, one green-sensitive, magenta-coupling silver halide emulsion layer and one red-sensitive, cyan-coupling silver halide emulsion layer; the yellow filter layer may be omitted.

The number and arrangement of the photosensitive layers may be varied in order to achieve specific results. For example, all high sensitivity layers may be grouped together in one package of layers and all low sensitivity layers may be grouped together in another package of layers in order to increase sensitivity (DE 25 30 645).

The hardener according to the invention is in particular added to the layer furthest away from the support. This layer should contain as little gelatine as possible or no gelatine, in order to avoid problems during casting.

The hardener according to the invention may, however, be distributed in more than one layer or in all layers. The total quantity amounts to 0.1 to 0.4 mol/g of total gelatine.

The substantial constituents of the photographic emulsion layers are binder, silver halide grains and colour couplers.

Details of suitable binders may be found in *Research Disclosure* 37254, part 2 (1995), page 286.

Details of suitable silver halide emulsions, the production, ripening and stabilisation thereof, may be found in *Research Disclosure* 37254, part 3 (1995), page 286 and in *Research Disclosure* 37038, part XV (1995), page 89.

Photographic materials with camera sensitivity conventionally contain silver bromide-iodide emulsions, which may optionally also contain small proportions of silver chloride. Photographic print materials contain either silver chloride-bromide emulsions containing up to 80 mol. % of AgBr or silver chloride-bromide emulsions containing more than 95 mol. % of AgCl.

Details relating to colour couplers may be found in *Research Disclosure* 37254, part 4 (1995), page 288 and in *Research Disclosure* 37038, part II (1995), page 80. The maximum absorption of the dyes formed from the couplers and the developer oxidation product is preferably within the following ranges: yellow coupler 430 to 460 nm, magenta coupler 540 to 560 nm, cyan coupler 630 to 700 nm.

In order to improve sensitivity, grain, sharpness and colour separation in colour photographic films, compounds are frequently used which, on reaction with the developer oxidation product, release photographically active compounds, for example DIR couplers which eliminate a development inhibitor.

Details relating to such compounds, in particular couplers, may be found in *Research Disclosure* 37254, part 5 (1995), page 290 and in *Research Disclosure* 37038, part XIV (1995), page 86.

Colour couplers, which are usually hydrophobic, as well as other hydrophobic constituents of the layers, are conventionally dissolved or dispersed in high-boiling organic solvents. These solutions or dispersions are then emulsified into an aqueous binder solution (conventionally a gelatine solution) and, once the layers have dried, are present as fine droplets (0.05 to 0.8 $\mu$m in diameter) in the layers.

Suitable high-boiling organic solvents, methods for the introduction thereof into the layers of a photographic material and further methods for introducing chemical compounds into photographic layers may be found in *Research Disclosure* 37254, part 6 (1995), page 292.

The non-photosensitive interlayers generally located between layers of different spectral sensitivity may contain agents which prevent an undesirable diffusion of developer oxidation products from one photosensitive layer into another photo-sensitive layer with a different spectral sensitisation.

Suitable compounds (white couplers, scavengers or DOP scavengers) may be found in *Research Disclosure* 37254, part 7 (1995), page 292 and in *Research Disclosure* 37038, part III (1995), page 84.

The photographic material may also contain UV light absorbing compounds, optical whiteners, spacers, filter dyes, formalin scavengers, light stabilisers, anti-oxidants, $D_{min}$ dyes, additives to improve stabilisation of dyes, couplers and whites and to reduce colour fogging, plasticisers (latices), biocides and others.

Suitable compounds may be found in *Research Disclosure* 37254, part 8 (1995), page 292 and in *Research Disclosure* 37038, parts IV, V, VI, VII, X, XI and XIII (1995), pages 84 et seq.

Further hardeners may be used in addition to the hardeners according to the invention.

Suitable hardener substances may be found in *Research Disclosure* 37254, part 9 (1995), page 294 and in *Research Disclosure* 37038, part XII (1995), page 86.

Once exposed with an image, colour photographic materials are processed using different processes depending upon their nature. Details relating to processing methods and the necessary chemicals are disclosed in *Research Disclosure* 37254, part 10 (1995), page 294 and in *Research Disclosure* 37038, parts XVI to XXIII (1995), pages 95 et seq. together with example materials.

EXAMPLE 1

The following example is based on the layer structure below:

The layers stated below are applied in succession onto a cellulose triacetate film base provided with an anti-halation layer and a coupling layer. All stated quantities relate to 1 m$^2$. The quantity of silver applied is stated as the corresponding quantity of AgNO$_3$.

1. A less sensitive layer prepared from a red-sensitised silver bromide-iodide emulsion (5 mol. % AgI) prepared from 2.8 g of AgNO$_3$ and 2.5 g of gelatine containing dispersed therein 0.7 g of cyan coupler A, 0.3 g of cyan coupler B, 0.025 g of DIR coupler C and 0.075 g of red masking coupler D.
2. A high sensitivity layer prepared from a red-sensitised silver bromide-iodide emulsion (6 mol. % AgI) containing 1.9 g of AgNO$_3$, 2.0 g of gelatine, 0.21 g of cyan coupler A and 0.09 g of cyan coupler B.
3. An interlayer prepared from 0.7 g of gelatine.
4. A less sensitive layer prepared from a green-sensitised silver bromide-iodide emulsion (6 mol. % AgI) containing 2.3 g of AgNO$_3$, 2.6 g of gelatine containing dispersed therein 0.3 g of magenta coupler of the formula E, 0.3 g of magenta coupler F, 0.06 g of DIR coupler G and 0.09 g of yellow masking coupler H.
5. A high sensitivity layer prepared from a green-sensitised silver bromide-iodide emulsion (6 mol. % AgI) containing 2.6 g of AgNO$_3$, 2.2 g of gelatine and, dispersed therein, 0.25 g of magenta coupler E.
6. An interlayer prepared from 1.0 g of gelatine.
7. A Carey Lea silver filter layer with a colour density of 0.7 at a gelatine application of 1.0 g per m$^2$.
8. A less sensitive layer prepared from a blue-sensitised silver bromide-iodide emulsion (5 mol. % AgI) containing 0.95 g of AgNO$_3$, 2.0 g of gelatine and, dispersed therein, 1.6 g of yellow coupler of the formula J.
9. A high sensitivity layer prepared from a blue-sensitised silver bromide-iodide emulsion (6 mol. % AgI) containing 0.5 g of $AgNO_3$, 1.0 g of gelatine and, dispersed therein, 0.1 g of yellow coupler J.
10. An overcoat prepared from 1.2 g of gelatine.
11. An overcoat prepared from 0.25 g of gelatine with 3.3 mmol of hardener K.

In addition to this layer structure, described as sample 1, a sample 2 was produced in a similar manner which, instead of hardener K in the 11th layer, was combined with the corresponding quantity of hardener HM 2 according to the invention.

Both samples were exposed behind a graduated step wedge with green light and processed after development with N-ethyl-N-β-oxyethyl-3-methyl-p-phenylene-diamine (3.25 minutes at 38° C.) with subsequent bleach-fixing (see the process described by Ernest Ch. Gehret *British Journal of Photography*, 1974, page 597).

Both materials exhibited a swelling factor of 3.0, i.e. were identically adequately hardened. Neither sample exhibited any sign of delamination even after 5 minutes exposure to boiling water.

Two further samples were stored for 21 days under tropical conditions at 65° C. and 95% relative humidity before exposure and processing and then exposed with green light behind a graduated step wedge. Processing was performed as above.

|  | Storage | Sensitivity | $D_{min}$ | $D_{max}$ | Gradation |
|---|---|---|---|---|---|
| Sample 1 | fresh | 100 | 24 | 232 | 1.34 |
| Sample 1 | 65° C./95% | 90 | 66 | 200 | 0.98 |
| Sample 2 | fresh | 101 | 23 | 230 | 1.32 |
| Sample 2 | 65° C./95% | 100 | 26 | 228 | 1.30 |

As may clearly be seen from the values obtained, the hardeners according to the invention exhibit distinct advantages on storage under moist and hot climatic conditions.

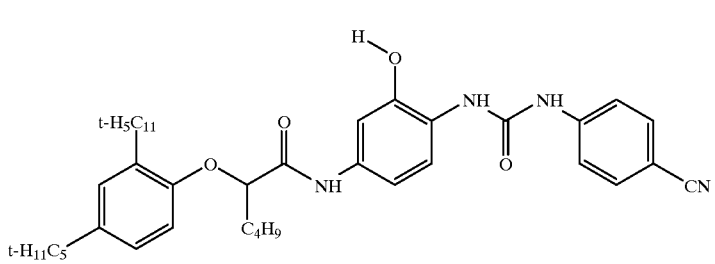

A

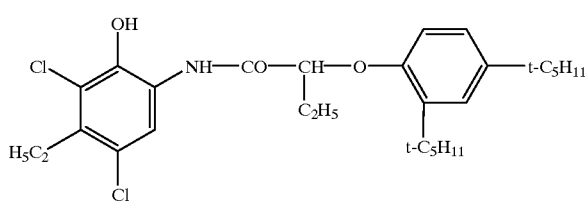

B

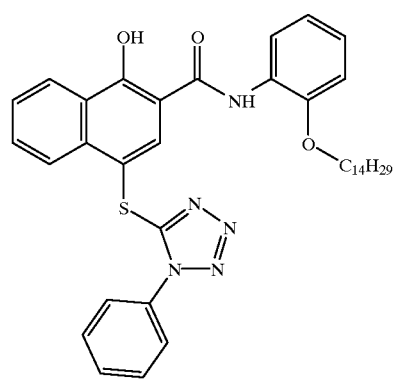

C

-continued
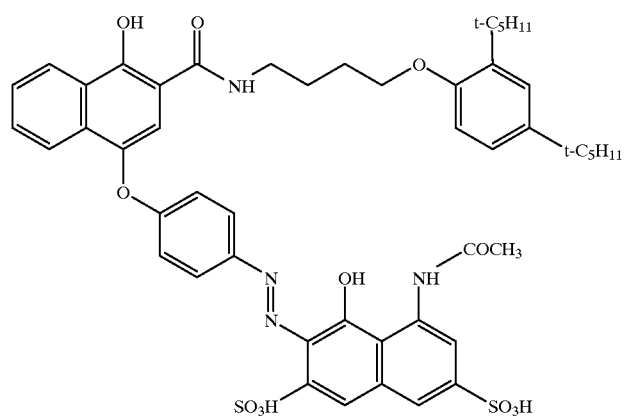
D
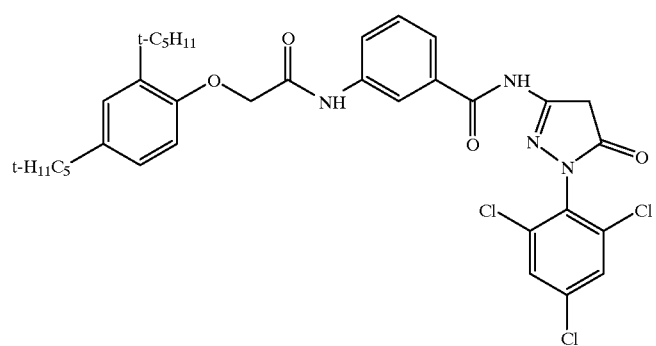
E
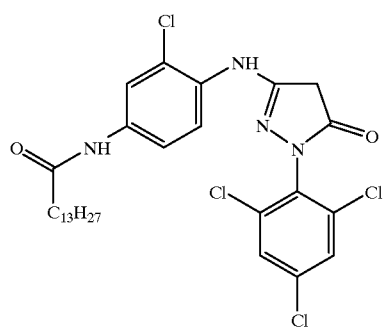
F

G
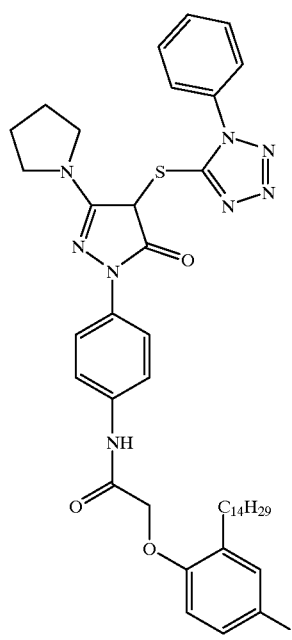
H
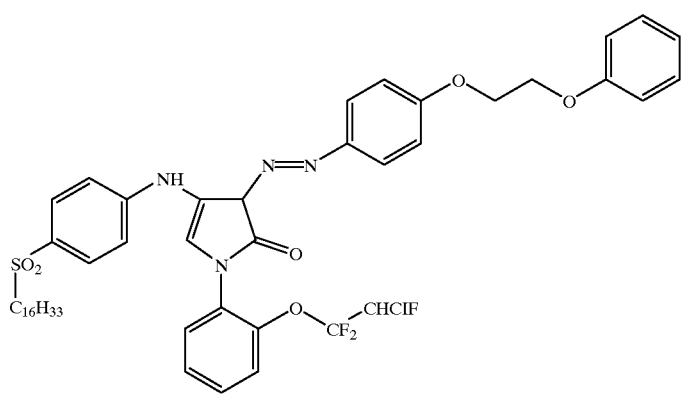
J
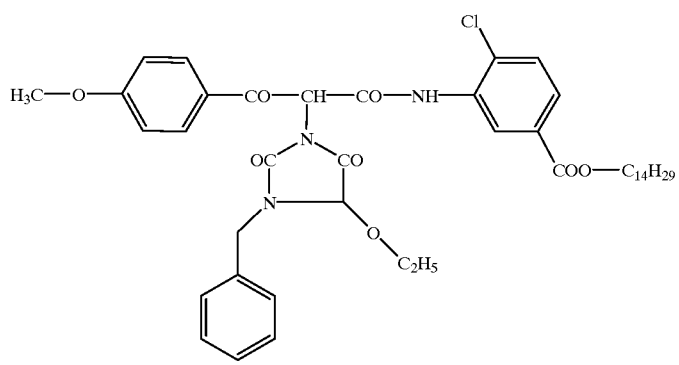
K
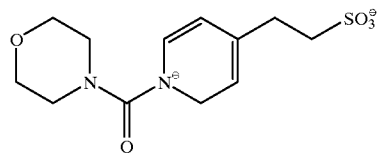

EXAMPLE 2

The following example of a colour negative film material is based on the layer structure below:

The layers stated below are applied in succession onto a cellulose triacetate film base provided with an anti-halation layer and a coupling layer. All stated quantities relate to 1 m$^2$. The quantity of silver applied is stated as the corresponding quantity of $AgNO_3$. All the silver halide emulsions were stabilised with 0.5 g of 4-hydroxy-6-methyl-1,3,3a,7-tetraazaindene per 100 g of $AgNO_3$.

Layer 1: (Anti-halo layer)
  Colloidal silver sol with 0.18 g of Ag
  0.30 g of UV absorber UV-1
  1.5 g of gelatine Layer 2: (Interlayer)
  Silver bromide-iodide emulsion (0.8 mol. % AgI); 0.15 g of $AgNO_3$
  0.15 g of dioctylhydroquinone
  0.11 g of coupler CY 1
  0.3 g of gelatine Layer 3: (1st red-sensitive layer)
  Red-sensitised silver bromide-iodide emulsion (5 mol. % AgI); 0.70 g of $AgNO_3$
  0.10 g of coupler CY 2
  0.30 g of coupler CY 3
  0.01 g of coupler CY 4
  1.2 g of gelatine Layer 4: (2nd red-sensitive layer)
  Red-sensitised silver bromide-iodide emulsion (10 mol. % AgI); 1.20 g of $AgNO_3$
  0.10 g of coupler CY 2
  0.05 g of coupler CY 3
  0.05 g of coupler CY 4
  0.90 g of gelatine Layer 5: (3rd red-sensitive layer)
  Red-sensitised silver bromide-iodide emulsion (10 mol. % AgI); 2.00 g of $AgNO_3$
  0.05 g of coupler CY 3
  0.15 g of coupler CY 5
  0.003 g of coupler DIR 1
  0.80 g of gelatine Layer 6: (Interlayer)
  0.05 g of gelatine Layer 7: (1st green-sensitive layer)
  Green-sensitised silver bromide-iodide emulsion (5 mol. % AgI); 0.50 g of $AgNO_3$
  0.30 g of coupler CM 1
  0.40 g of coupler MG 1
  0.50 g of coupler MG 2
  0.50 g of coupler DIR 2
  1.20 g of gelatine Layer 8: (2nd green-sensitive layer)
  Green-sensitised silver bromide-iodide emulsion (6 mol. % AgI); 1.00 g of $AgNO_3$
  0.25 g of coupler CM 1
  0.01 g of coupler MG 1
  0.01 g of coupler MG 2
  0.01 g of coupler DIR 2
  1.70 g of gelatine Layer 9: (3rd green-sensitive layer)
  Green-sensitised silver bromide-iodide emulsion (10 mol. % AgI); 1.50 g of $AgNO_3$
  0.015 g of coupler MG 1
  0.07 g of coupler CM 1
  0.002 g of coupler DAR 1
  1.00 g of gelatine Layer 10: (Yellow filter layer)
  0.05 g of colloidal silver sol
  0.03 g of dioctylhydroquinone
  1.00 g of gelatine Layer 11: (1 st blue-sensitive layer)
  Silver bromide-iodide emulsion (5 mol. % AgI); 0.30 g of $AgNO_3$
  0.70 g of coupler Y 1
  0.03 g of coupler DIR 3
  1.40 g of gelatine Layer 12: (2nd blue-sensitive layer)
  Silver bromide-iodide emulsion (5 mol. % AgI); 0.30 g of $AgNO_3$
  0.25 g of coupler Y 1
  0.60 g of gelatine Layer 13: (Micrate layer)
  Silver bromide-iodide emulsion (2 mol. % AgI); 0.40 g of $AgNO_3$
  0.10 g of gelatine Layer 14: (3rd blue-sensitive layer)
  Silver bromide-iodide emulsion (10 mol. % AgI); 0.80 g of $AgNO_3$
  0.20 g of coupler Y 1
  0.50 g of gelatine Layer 15: (1st protective layer)
  0.14 g of UV absorber UV-1
  0.20 g of UV absorber UV-2
  0.40 g of gelatine Layer 16: (2nd protective layer)
  0.95 g of hardener K
  0.23 g of gelatine In addition to this layer structure, described as sample 3, a sample 4 was produced in a similar manner which, instead of hardener K, was hardened with the corresponding quantity of hardener HM 1 according to the invention. Both samples were exposed behind a graduated step wedge with green light and processed after development using an AP 72 process (c.f. the process described by E. Ch. Gehret: *Brit. Journ. Photogr.*, 1974, page 597).

One specimen of each of samples 3 and 4 was stored for 21 days at 65° C. and 95% relative humidity before exposure and processing.

|  | Storage | Sensitivity | $D_{min}$ | $D_{max}$ | Gradation |
|---|---|---|---|---|---|
| Sample 3 | fresh | 100 | 39 | 250 | 1.56 |
| Sample 3 | 21 d, 65° C./95% | 78 | 88 | 195 | 0.88 |
| Sample 4 | fresh | 99 | 32 | 245 | 1.60 |
| Sample 4 | 21 d, 65° C./95% | 97 | 37 | 235 | 1.45 |

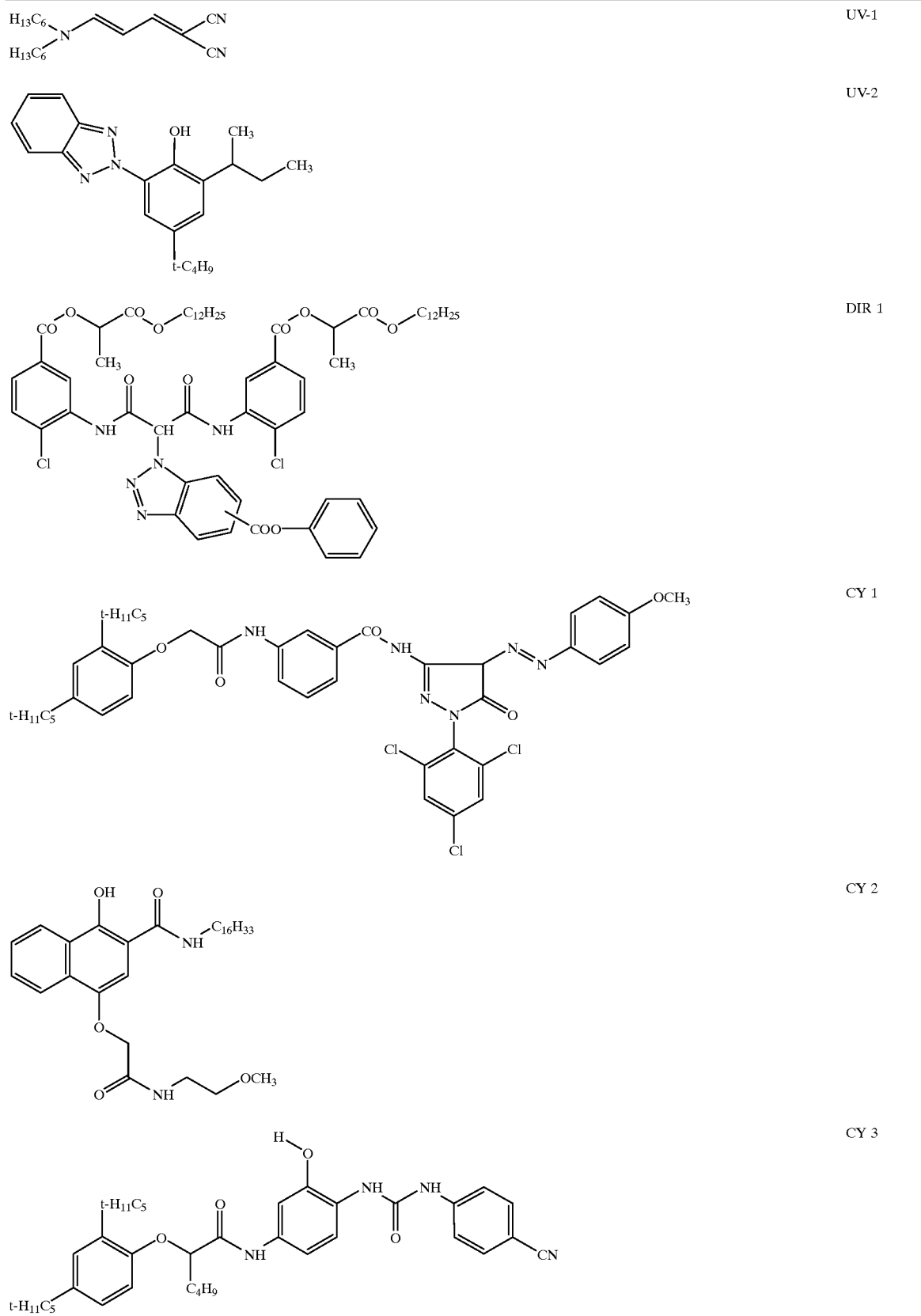

-continued
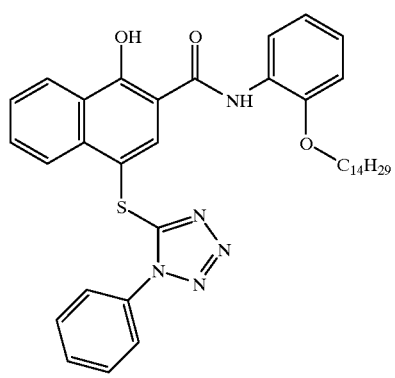
CY 4
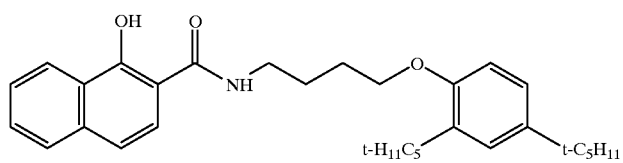
CY 5
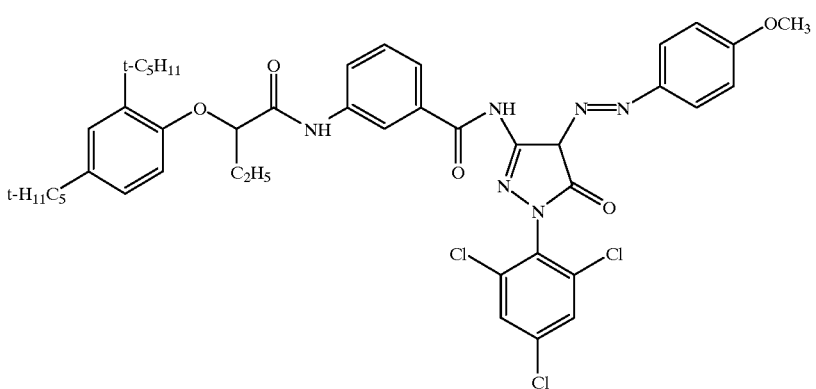
MG 1
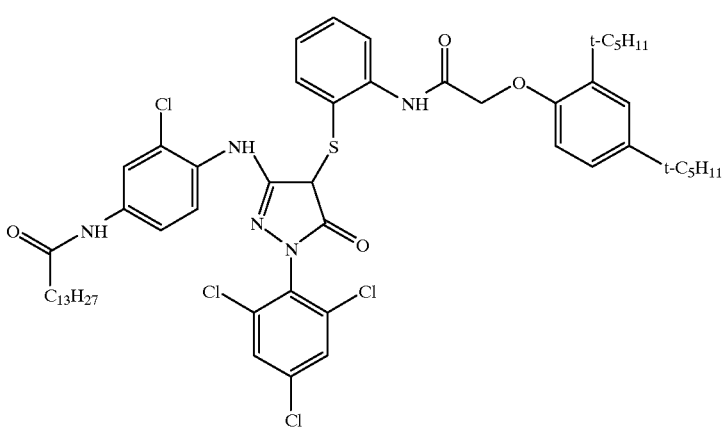
CM 1

-continued
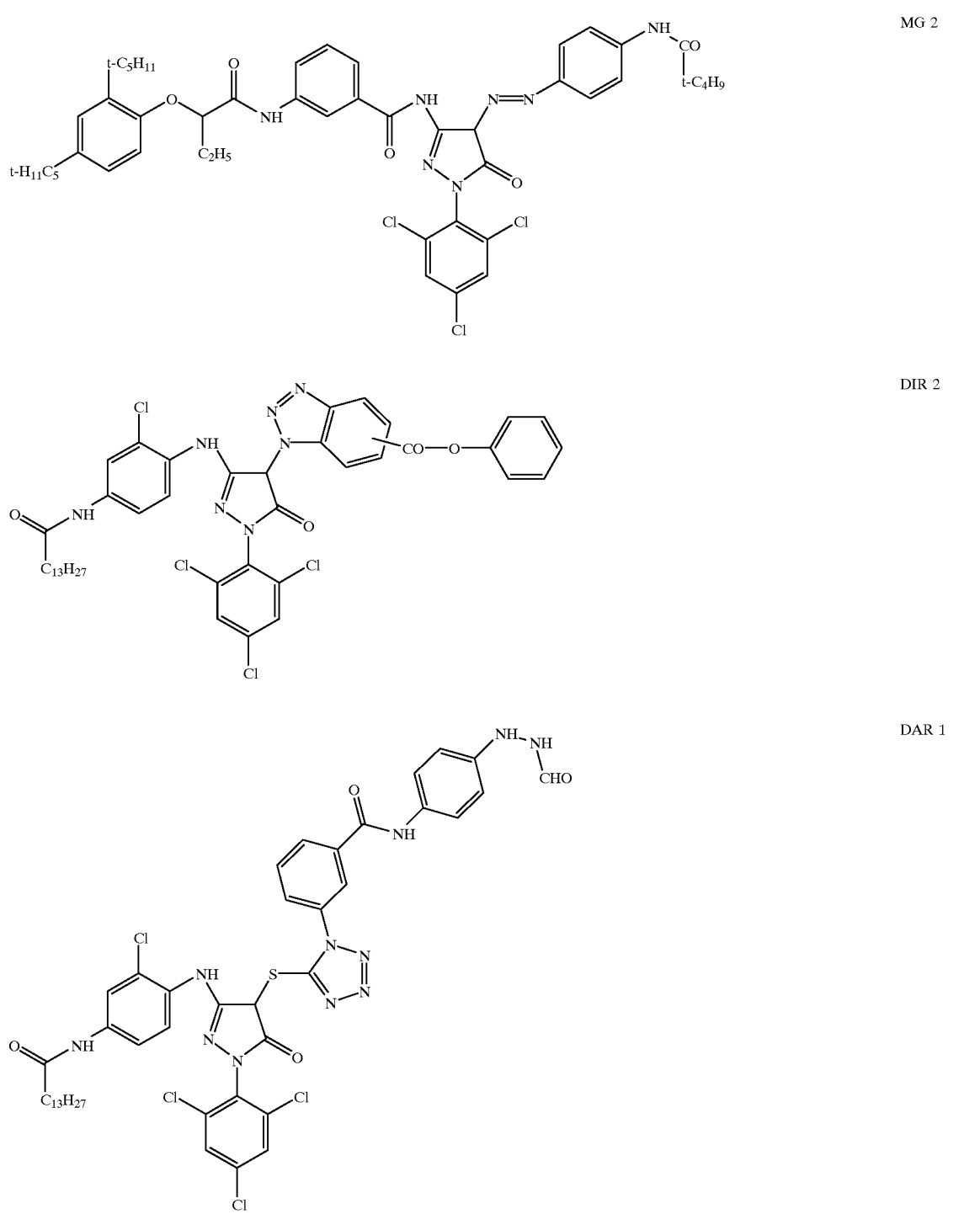

-continued

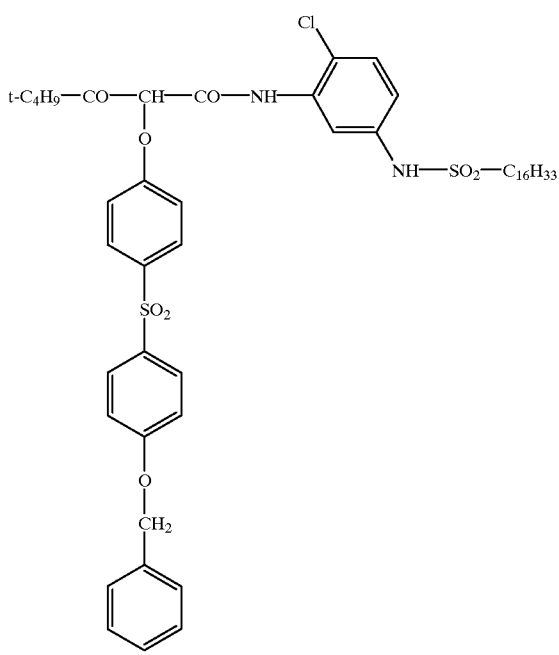

Y1

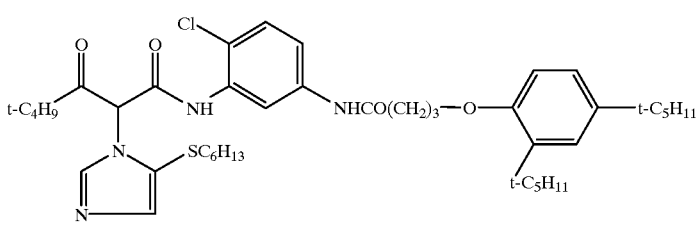

DIR 3

We claim:

1. A compound of the formula

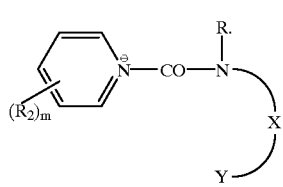

in which

R₁ is an alkyl group,

R₂ is an alkylene group with 1 to 4 C atoms substituted by $SO_3^\ominus$ or $COO^\ominus$ or is a $-SO_3^\ominus-$ or $-COO^\ominus-$ group, m is 1 to 3, Y is an ester group, an epoxide group, a vinylsulfonyl group, an isocyanate group, Br, Cl, CN, a methylol group, an urethane group or a carbon—carbon double bond substituted on one of its carbon atoms by CN, NO, CF₃, CO or SO₂, and when X is a phenylene group, Y is located on said phenlylene in the ortho position to the N atom attached to the R₁ and X is an alkelene or phenylene group.

2. A compound of the formula

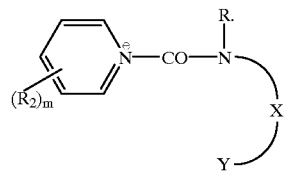

in which

R₁ is an alkyl group,

R₂ is an alkylene group with 1 to 4 C atoms substituted by $SO_3^\ominus$ or $COO^\ominus$ or is a $-SO_3^\ominus-$ or $-COO^\ominus-$ group, m is 1 to 3, Y is an ester group, an epoxide group, a vinylsulfonyl group, an isocyanate group, Br, Cl, CN, a methylol group or an urethane group and when X is a phenylene group, Y is located on said phenylene in the ortho position to the N atom attached to the R₁; and X is an alkylene or phenylene group.

3. The compound as claimed in claim 1, wherein m is 1.
4. The compound as claimed in claim 2, wherein m is 1.
5. The compound according to claim 1, wherein X is an alkylene group with 2 to 5 C atoms or a group of the formula

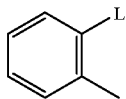

wherein L is linked to Y and means a single bond, an alkylene group with 1 to 3 C atoms or —SO$_2$—R$_3$, wherein the SO$_2$ group is attached to the phenyl residue and R$_3$ denotes an alkylene group with 1 to 3 C atoms.

6. A compound selected from the group consisting of

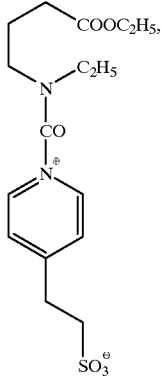

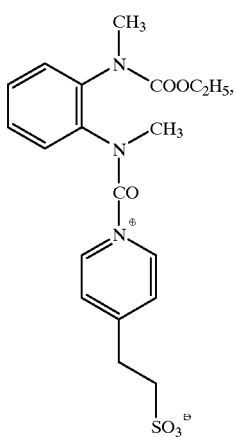

and

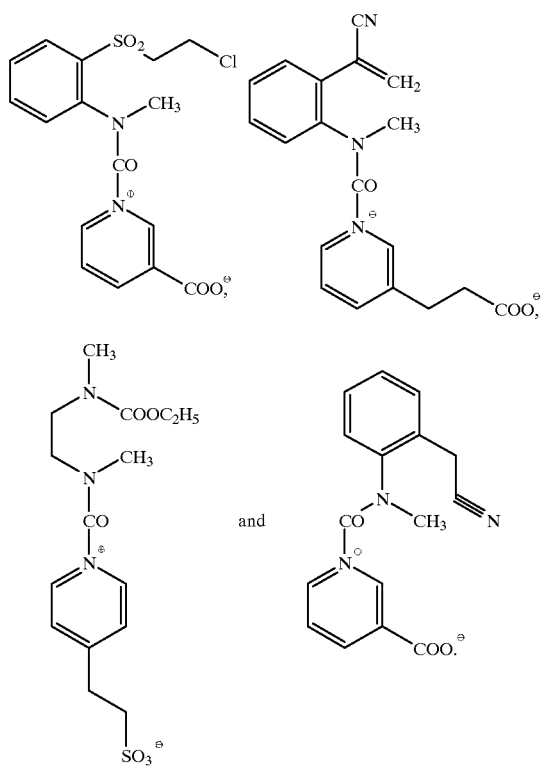

* * * * *